US00PP29432P2

(12) United States Plant Patent
Horvath

(10) Patent No.: US PP29,432 P2
(45) Date of Patent: Jun. 26, 2018

(54) ***CAREX PENSYLVANICA* PLANT NAMED 'STRAW HAT'**

(50) Latin Name: *Carex pensylvanica*
Varietal Denomination: Straw Hat

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days. days.

(21) Appl. No.: 14/998,925

(22) Filed: Mar. 7, 2016

(51) Int. Cl.
*A01H 5/00* (2018.01)

(52) U.S. Cl.
USPC ..... Plt./384

(58) Field of Classification Search
USPC ..... Plt./384, 373
CPC ... A01H 5/12; A01H 5/00; A01H 5/02; A01H 5/04; A01H 5/10
See application file for complete search history.

(56) References Cited

PUBLICATIONS

Emerald Coast Growers Starter Plants 2015-2016, retrieved on May 17, 2017, retrieved from the Internet at <http://www.ecgrowers.com/v/vspfiles/brochures/ecg_2015-16_catalog.pdf> pp. 1-5, 11, 87.*

* cited by examiner

*Primary Examiner* — June Hwu

(57) ABSTRACT

A new, distinct *Carex pensylvanica* plant as illustrated and described characterized larger florets giving the plant a showier floral display to be unique and stable.

2 Drawing Sheets

Latin name: *Carex pensylvanica.*
Cultivar name: 'Straw Hat'.

BACKGROUND OF THE INVENTION

The present invention relates to a new form of *Carex pensylvanica* plant named 'Straw Hat'. 'Straw Hat' is an open pollination seedling of an unnamed *Carex pensylvanica*, not patented, characterized larger florets giving the plant a showier floral display to be unique and stable. The new plant was selected as a by the inventor as part of an on going grass breeding program since 2009 at a wholesale perennial nursery in Hebron, Ill. in 2010. The selection of this plant was due to larger florets giving the plant a showier floral display. Asexual, vegetative division propagation has been the only means of reproduction. Propagation has taken place at a nursery in Hebron, Ill. since 2011. In 2011 we planted 60 plants in pots. To date these plants have remained uniform in height. The new *Carex pensylvanica* has shown to be stable and identical in reproduction to the parent after making over 3000 vegetative divisions from 2011 to 2015. No plants of *Carex pensylvanica* 'Straw Hat' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

In the following description, color references are made to The Royal Horticultural Society Colour Chart (2001). The following traits have been repeatedly observed and represent the characteristics of the new cultivar. The new *Carex*

*pensylvanica* has not been observed under all possible environmental conditions. These attributes in combination distinguish 'Straw Hat' from all other selections of *Carex pensylvanica* known to the Inventor. The new *Carex pensylvanica* plant named 'Straw Hat' has shown the larger florets giving the plant a showier floral display to be unique and stable.

Plants of the new *Carex* can be compared to plants of *Carex pensylvanica* the species, not patented. 1. The new *Carex pensylvanica* has larger, 10 mm wide florets, while florets of the species are 2-3 mm wide. 2. The new *Carex* has a florets that emerge a week or two earlier compared to the species. 3. The new *Carex pensylvanica* also has larger achene or seed measuring 3 mm long compared to the species which measure 1.5-2 mm long.

DESCRIPTION OF PHOTOGRAPHS

The accompanying colored photographs illustrate the overall appearance and distinct characteristics of two year-old plants as grown in a garden outdoors in Hebron, Ill., USA.

Figure 1:
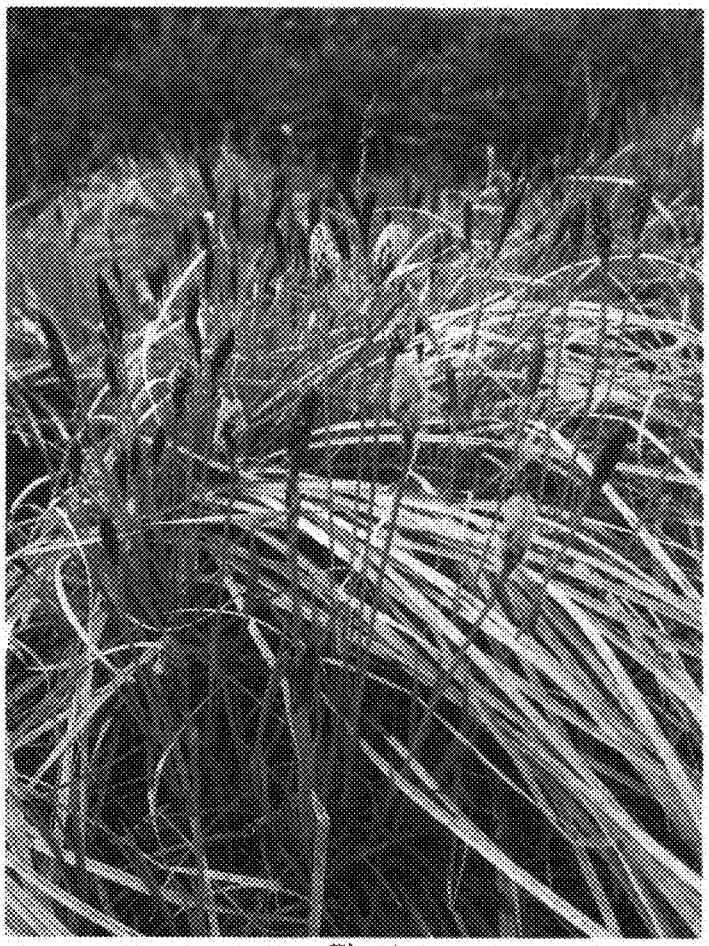

FIG. 1. Shows a plant beginning to bloom in April on a 2 year old plant.

Figure 2:
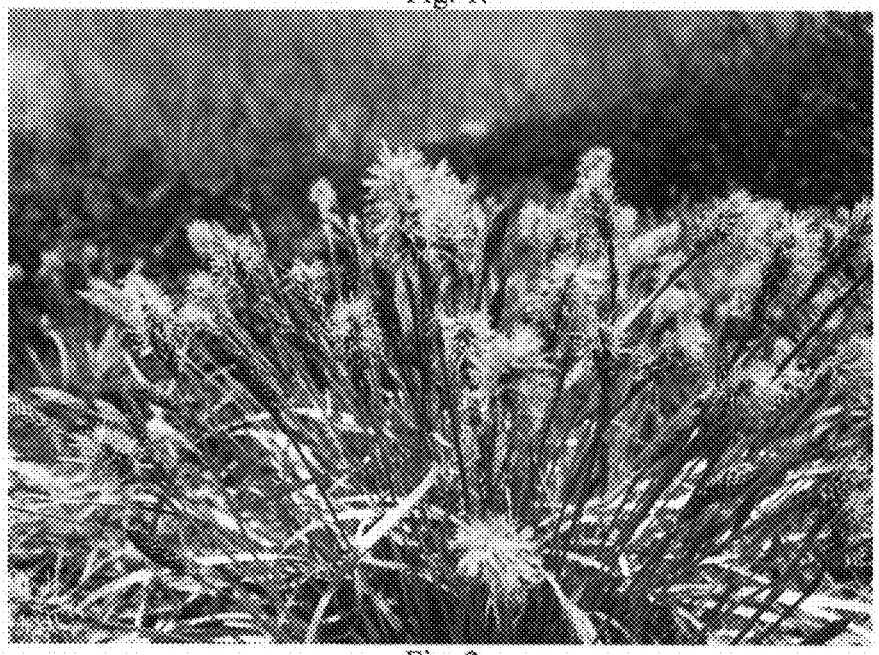

FIG. 2. Shows the appearance in full flower in May on a 2 year old plant.

Figure 3:
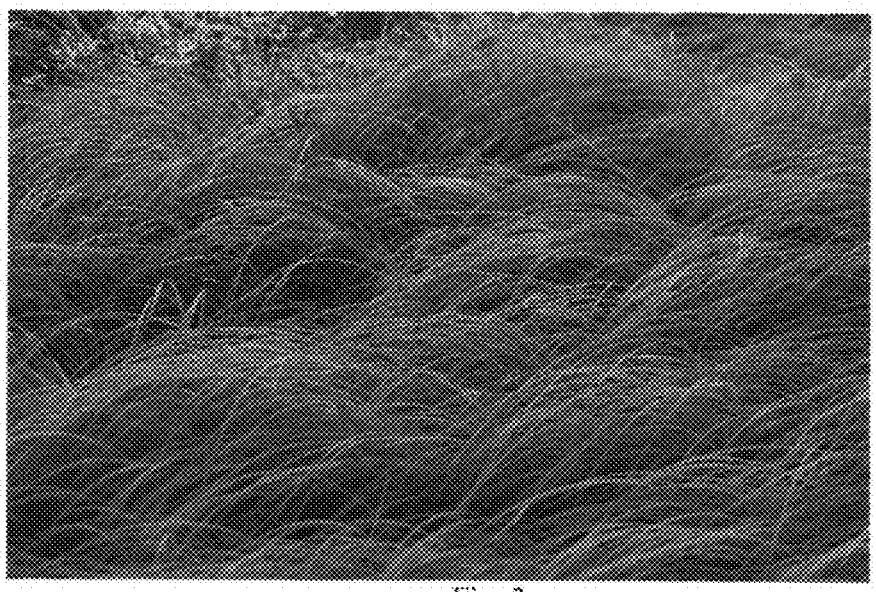

FIG. 3. Shows the foliage in June on a 2 year old plant.

DETAILED BOTANICAL DESCRIPTION

In the following description, color references are made to The Royal Horticultural Society Colour Chart (2001). The plant herein described is a two year old planting grown in full sun and irrigated in Hebron, Ill.

Botanical classification: *Carex pensylvanica* plant named 'Straw Hat'.

Parentage: Unnamed *Carex pensylvanica* seedling.

Propagation: Vegetative division.

Culture: Grows best in part shade in well drained to dry soil.

Growth rate: Moderate.

Plant type: Deciduous perennial grass, growing in culms 16 cm tall and 30 cm wide.

Plant description: Overall habit of the new *Carex pensylvanica* is tufted basal mounds that are stoloniferous with arching flower stems beginning in April. Vigor is moderate.

*Plant height.*—16 cm.

*Plant width.*—30 cm.

*Flower stem diameter.*—2 mm.

*Flower stem length.*—15 cm.

Foliage:

*Sheath color.*—Similar to the species with colors starting at 155 C in spring and changing to 184 C in fall.

*Sheath size and shape.*—30 mm long and 2 mm wide, truncate to deeply cleft becoming fibrous.

*Shape.*—Linear, arching blade.

*Petiole.*—None.

*Apex.*—Attenuate.

*Aspect.*—Upright, then arching down to the ground.

*Leaf venation.*—Parallel, color matches leaf color.

*Margins.*—Entire.

*Leaf persistence.*—Deciduous with some foliage remaining green 146 A while some turns close to 156 D over winter.

*Leaf size.*—Length 28 cm, width 2 mm.

*Leaf number.*—4 per culm, 140 per plant.

*Leaf arrangement.*—Equitant emerging from the center, sheathed to the base.

*Leaf durability to stress.*—Moderate.

*Adaxial and abaxial leaf description.*—Surface — glabrous, smooth, color — upon emerging is 146 B and upon maturing is 146 A.

Floret description:

*Inflorescence type.*—Terminal spikes of staminate and lateral pistillate spikelets, slightly separated by 5 mm.

*Overall size of a mature inflorescence.*—1 cm wide and 2 cm long.

*Floret bud.*—Narrow ovate shape, 3 mm wide, 11 mm long.

*Floret scale size and shape.*—Similar to the species 1 mm wide and 4 mm long, obtuse to acuminate, margin entire, apex acute, surface smooth, and dull in appearance.

*Floret scale color.*—Emerging 166 A.

*Spikelet aspect.*—Upright.

*Spikelet shape and persistence.*—Narrow ovate, persistent.

*Inflorescence stem color.*—146 B.

*Inflorescence color.*—Upon opening the color is 9 D and maturing to 9 C.

*Flower number.*—Approximately 1 florets per spikelet, about 80% are staminate and 20% are pistillate.

*Individual spikelets size.*—Overall 10 mm wide, 15 mm long.

*Spikelet color.*—9 C.

*Staminate florets.*—1 glume, 1 lemma, 8-10 in number, held terminally, 10 mm wide, 15 mm long, color 9 C.

*Pistillate spikes.*—1 lemma, no glume, 1-2 held laterally, 1 mm wide, 5 mm long, lanceolate in shape, margin entire, apex acute, color both upper and lower surface 10 B, surface smooth, dull in appearance.

*Perigynium.*—3-4 mm long and 1-2 mm wide, orbicular, trigonous, 2 keeled, color 146 B.

*Rachis.*—15 mm long 1 mm in diameter, held upright, string, color 146 B.

*Lastingness of the inflorescence.*—Flower last around 7 days.

*Fertility.*—Fertile.

*Bloom period and duration.*—Mid April through May.

*Scent.*—No scent noticed.

*Root description.*—Short stolons with dense fibrous roots, color N 77 A, 1-1.5 mm wide, moderately branched.

*Gynoecium.*—3 pistils, 2-3 mm in length, stigma is fimriate, style less than 1 mm in length, ovary color 146 B.

*Androcoecium.*—3 staems, basifixed, 2-3 mm in length, color 9 C.

*Fruit.*—Seed appears identical to the species *Carex pensylvanica* which are 2 mm long, 1 mm wide but slightly larger 2-3 mm long and 1-2 mm wide.

*Hardiness.*—USDA Zones 4-9.

*Diseases and pests resistance.*—Plants are not susceptible to any major pests or diseases.

*Culture.*—Grows best in part shade in well drained average to dry soils.

I claim:

1. A new, distinct *Carex pensylvanica* plant as illustrated and described characterized larger florets giving the plant a showier floral display to be unique and stable.

* * * * *